(12) United States Patent
Mitchell et al.

(10) Patent No.: US 9,890,634 B2
(45) Date of Patent: Feb. 13, 2018

(54) SYSTEMS AND METHODS FOR REAL-TIME MEASUREMENT OF GAS CONTENT IN DRILLING FLUIDS

(71) Applicant: Halliburton Energy Services, Inc., Houston, TX (US)

(72) Inventors: Ian David Campbell Mitchell, The Woodlands, TX (US); Mathew Dennis Rowe, Lafayette, LA (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 269 days.

(21) Appl. No.: 14/889,940

(22) PCT Filed: Nov. 10, 2014

(86) PCT No.: PCT/US2014/064828
§ 371 (c)(1),
(2) Date: Nov. 9, 2015

(87) PCT Pub. No.: WO2016/076825
PCT Pub. Date: May 19, 2016

(65) Prior Publication Data
US 2016/0290131 A1 Oct. 6, 2016

(51) Int. Cl.
*E21B 49/00* (2006.01)
*E21B 49/08* (2006.01)
(Continued)

(52) U.S. Cl.
CPC .......... *E21B 49/005* (2013.01); *E21B 21/067* (2013.01); *E21B 47/102* (2013.01);
(Continued)

(58) Field of Classification Search
CPC .............. G01N 21/85; G01N 21/8507; G01N 33/0004; G01N 33/0006; G01N 33/0008; G01N 33/004; G01N 33/0047; E21B 49/00; E21B 49/003; E21B 49/005; E21B 49/08; E21B 49/081; E21B 49/083;
(Continued)

(56) References Cited

U.S. PATENT DOCUMENTS 4,492,862 A  1/1985 Grynberg et al.
4,994,671 A  2/1991 Safinya et al.
(Continued)

FOREIGN PATENT DOCUMENTS

WO  8202573 A1  8/1982
WO  2015047247 A1  4/2015

OTHER PUBLICATIONS

International Search Report and Written Opinion for PCT/US2014/064828 dated Aug. 7, 2015.

*Primary Examiner* — Gordon J Stock, Jr.
(74) *Attorney, Agent, or Firm* — McDermott Will & Emery LLP

(57) ABSTRACT

Measuring the amount of individual gases in drilling fluids in real-time may be performed with optical computing devices that are calibrated in real-time or periodically with gas analysis devices to provide more accurate gas content measurements. In some instances, one or more drilling or completion parameters may be altered in response thereto the concentration or change in concentration of individual gases in drilling fluids.

20 Claims, 4 Drawing Sheets

(51) Int. Cl.
*E21B 21/06* (2006.01)
*G01N 33/00* (2006.01)
*E21B 47/10* (2012.01)
*G01N 21/84* (2006.01)
*G01N 21/85* (2006.01)

(52) U.S. Cl.
CPC ............ *E21B 49/08* (2013.01); *E21B 49/087* (2013.01); *G01N 33/004* (2013.01); *G01N 33/0006* (2013.01); *G01N 33/0047* (2013.01); *E21B 21/062* (2013.01); *G01N 21/8507* (2013.01); *G01N 2021/8405* (2013.01); *G01N 2021/8411* (2013.01); *G01N 2021/8416* (2013.01)

(58) Field of Classification Search
CPC .... E21B 49/084; E21B 49/086; E21B 49/087; E21B 49/088; E21B 49/19; E21B 7/04; E21B 47/102; E21B 21/062; E21B 21/063; E21B 21/067
See application file for complete search history.

(56) References Cited

U.S. PATENT DOCUMENTS

| | | | |
|---|---|---|---|
| 5,167,149 A | 12/1992 | Mullins et al. | |
| 6,178,815 B1 | 1/2001 | Felling et al. | |
| 6,974,705 B1 | 12/2005 | Brumboiu et al. | |
| 6,995,360 B2 | 2/2006 | Jones et al. | |
| 7,124,030 B2 | 10/2006 | Ellis | |
| 7,336,356 B2 | 2/2008 | Vannuffelen et al. | |
| 7,392,138 B2 | 6/2008 | Frechin et al. | |
| 7,576,856 B2 | 8/2009 | DiFoggio | |
| 8,352,205 B2 * | 1/2013 | Myrick | G01J 3/02 250/252.1 |
| 8,448,495 B2 | 5/2013 | Breviere et al. | |
| 8,632,625 B2 | 1/2014 | DeGreeve et al. | |
| 8,823,939 B2 * | 9/2014 | Freese | G01N 21/17 356/433 |
| 9,542,511 B2 * | 1/2017 | Chen | G06F 19/704 |
| 9,568,641 B2 * | 2/2017 | Simcock | E21B 47/00 |
| 9,612,361 B2 * | 4/2017 | Chen | E21B 47/102 |
| 2006/0142955 A1 | 6/2006 | Jones et al. | |
| 2011/0313670 A1 | 12/2011 | DeGreeve et al. | |
| 2013/0033702 A1 | 2/2013 | Tunheim et al. | |
| 2013/0283888 A1 | 10/2013 | DiFoggio | |
| 2013/0311096 A1 * | 11/2013 | Greer | G01N 30/88 702/9 |
| 2015/0300945 A1 * | 10/2015 | Gao | G01N 21/274 702/104 |
| 2015/0369043 A1 * | 12/2015 | Pelletier | G01J 3/42 356/416 |
| 2016/0102510 A1 * | 4/2016 | Mitchell | E21B 47/102 175/24 |

* cited by examiner

SYSTEMS AND METHODS FOR REAL-TIME MEASUREMENT OF GAS CONTENT IN DRILLING FLUIDS

BACKGROUND

The present disclosure relates to systems and methods for measuring the gas content in drilling fluids.

During the drilling of a hydrocarbon-producing well, a drilling fluid or "mud" is continuously circulated from the surface down to the bottom of the wellbore being drilled and back to the surface again. The drilling fluid serves several functions, one of them being to transport wellbore cuttings up to the surface where they are separated from the drilling fluid. Another function of the drilling fluid is to cool the drill bit and provide hydrostatic pressure on the walls of the drilled borehole to prevent wellbore collapse and the resulting influx of gas or liquid from the formations being drilled.

Analyzing the drilling fluid as it returns to the surface is recognized in the oil and gas industry as an important first appraisal of a potential hydrocarbon-bearing reservoir zone, thereby providing important data to guide subsequent evaluation and testing. Such analysis and testing is commonly referred to as "mud logging" analysis. Through mud logging, reservoir zones can be evaluated while they are being initially penetrated by measuring the formation gases present in the drilling fluid as it returns to the surface. The presence and concentration of hydrocarbon and non-hydrocarbon gases in drilling fluids relative to the depth can be used in designing stimulation operations and production operations, as well as in the assessment.

Mud logging analysis of drilling fluids is typically conducted off-line using laboratory analyses which require the extraction of a sample of the drilling fluid and a subsequent controlled testing procedure usually conducted at a separate location. Because the characteristics of the extracted sample of the drilling fluid often changes during the lag time between collection and analysis, off-line, retrospective analyses can be unsatisfactory for determining true characteristics of a drilling fluid.

Additionally, some mud logging analyses take hours to days to complete. Therefore, the drilling operation is often finished prior to completion of the analysis. As a result, proactive control of drilling operations cannot take place, at least without significant process disruption occurring while awaiting the results of the mud logging analyses.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
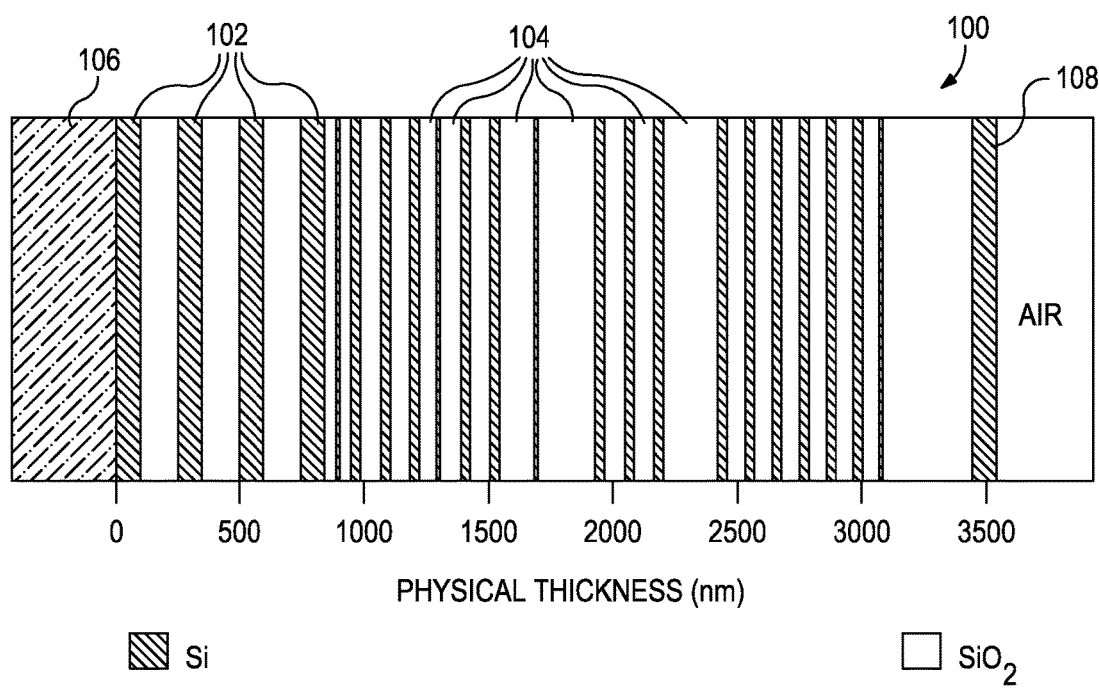
FIG. 1 illustrates an exemplary integrated computation element, according to one or more embodiments.

The present disclosure relates to systems and methods for measuring the gas content in drilling fluids in real-time using optical computing devices that can be calibrated in real-time, which may provide for more accurate gas content measurements. The gas content measurements may be used for adjusting one or more drilling parameters in response thereto.

The exemplary systems and methods described herein employ various configurations and arrangements of optical computing devices, also commonly referred to as "opticoanalytical devices," for the real-time or near real-time analysis of a material of interest. In operation, the exemplary systems and methods may be useful and otherwise advantageous in determining one or more properties or characteristics of the fluid, such as the type and concentration of one or more gases present within the fluid. This may allow for qualitative and/or quantitative analyses of the fluid to occur without having to extract a sample and undertake time-consuming analyses of the sample at an off-site laboratory, which may be particularly advantageous in real-time mud logging.

The systems and methods disclosed herein may be suitable for use in the oil and gas industry since the described optical computing devices provide a cost-effective, rugged, and accurate means for monitoring oil/gas-related fluids, such as drilling fluids. In particular, the systems and methods may prove advantageous for use in mud logging gas analysis, thereby providing a stream of continuous data on the hydrocarbon and non-hydrocarbon gas species that may be encountered while drilling into subterranean formations. When the drilling fluid returns to the surface, for example, it may contain hydrocarbons (and other compounds) contained within the rock that has been drilled as well as additional hydrocarbons that have leaked into the wellbore from the surrounding rock formation. The real-time measurement of the abundance of these gas compounds will yield information on the hydrocarbon content of the rock.

However, in some instances, it may be difficult to measure some gas species present in the drilling fluid, for example, because of a low concentration of the gas of interest, because of a high concentration of another gas (e.g., methane) that interferes with detection (e.g., having an overlapping spectrum), or a combination thereof. Accordingly, in some instances, optical computing devices optionally in combination with other analytical devices may be used for analyzing of reference gases in the drilling fluid and each gas of interest in the gas extracted from the drilling fluid. Then, the concentration of the reference gases in the drilling fluid and in the extracted gas can be compared and related with a correction factor or correction function. Then, the correction factor/function may be used to extrapolate the concentration of each gas of interest in the drilling fluid from the concentration of each gas of interest in the extracted gas. Such methods or similar methods may provide more accurate mud logging in real-time at the well site.

In some embodiments, analysis of the gas extracted from the drilling fluid may be performed on the surface, outside of the stringent downhole environmental conditions (high pressure, high temperature, and strong vibrations). Accordingly, specialized and sophisticated measurement techniques may be available to analyze the extracted gas, such as optical measurement techniques, gas chromatography, and the like. Moreover, a plurality of measurement techniques may be used at the surface on the extracted gas sample when the signals from two different compounds interfere with one another using a single measurement technique. For example, when the optical signature of two compounds interferes with one another, a gas chromatographer may be able to distinctly separate each of the two compounds and provide a precise measurement value for the two. In this regard, systems and methods consistent with the present disclosure enable obtaining a measurement of a gas concentration in the drilling fluid at the downhole location, based on the measurement of the gas concentration in the extracted gas at the surface.

Information regarding the hydrocarbon content of the rock may be provided to a well operator for interpretation and consideration and, if required, the well operator may alter various drilling or completion parameters in response thereto. For instance, depending on what types and concentrations of gases are detected within the rock being drilled, a well operator may adjust production valves and/or choke settings in order to regulate the progress of the drilling operation and also minimize wellbore kick through early kick detection. In other cases, the well operator may alter mud properties in an effort to optimize drilling efficiency or formation evaluation efficiency. Other drilling and completion parameters that may be altered by a well operator upon consideration of the data include changing a planned cementing and/or casing program and optimizing a well completion design.

In some cases, the data may reveal excessive amounts of hazardous or otherwise toxic gases being returned to the surface. Such gases may pose a potential health hazard to rig workers and the surrounding environment. In such cases, the well operator may proactively reduce the amount of hazardous/toxic gases by introducing one or more remedial additives or components to the drilling fluid.

In other cases, the data may indicate an increased amount of viable hydrocarbons in the drilled borehole, such as in a particular lateral trajectory of the wellbore. In such cases, the well operator may manipulate the well plan and/or geosteering so that the resulting wellbore is formed substantially in and through the observed hydrocarbon-rich strata or region. In other words, the planned trajectory of the well path may be manipulated or otherwise altered by geosteering the drilling equipment such that the borehole penetrates a larger portion of the hydrocarbon-rich strata than would have otherwise been penetrated.

As used herein, the term "fluid" refers to any substance that is capable of flowing, including particulate solids, liquids, gases, slurries, emulsions, powders, muds, mixtures, combinations thereof, and the like. In some embodiments, the fluid is a drilling fluid or drilling "mud," including water-based drilling fluids, oil-based drilling fluids, synthetic drilling fluids, and the like. In other embodiments, the fluid may be a completion fluid or a clean-up fluid such as, but not limited to, fresh water, saltwater (e.g., water containing one or more salts dissolved therein), brine (e.g., saturated salt water, chloride salts, bromide salts, combinations thereof, etc.), seawater, a spacer fluid, base fluids, or other treatment fluids known in the art.

As used herein, the term "characteristic" refers to a chemical, mechanical, or physical property of the fluid. A characteristic of the fluid may include a quantitative value or concentration of one or more chemical constituents or compounds present within the fluid. Such chemical constituents may be referred to herein as "analytes." Illustrative characteristics of a substance that can be monitored with the optical computing devices disclosed herein can include, for example, chemical composition (e.g., identity and concentration in total or of individual components or compounds), phase presence (e.g., gas, oil, water, etc.), impurity content, pH, alkalinity, viscosity, density, ionic strength, total dissolved solids, salt content (e.g., salinity), porosity, opacity, bacterial content, total hardness, combinations thereof, state of matter (solid, liquid, gas, emulsion, mixtures, etc.), and the like.

Moreover, the phrase "characteristic of interest of/in a fluid" may be used herein to refer to the concentration or characteristic of a gas contained in or otherwise entrained within the fluid. Exemplary gases that may be monitored or otherwise measured with the optical computing devices as contained within a drilling fluid, for example, include, but are not limited to, methane, ethane, propane, n-butane, n-pentane, iso-butane, iso-pentane, neo-pentane, benzene, toluene, carbon dioxide, carbon monoxide, hydrogen sulfide, acetic acid, argon, helium, oxygen, nitrogen, water, hydrogen, carbonyl sulfide, carbon disulfide, and any combination thereof.

As used herein, the term "flow path" refers to a route through which a fluid is capable of being transported between at least two points. In some cases, the flow path need not be continuous or otherwise contiguous between the two points. Exemplary flow paths include, but are not limited to, a flow line, a pipeline, production tubing, drill string, work string, casing, a wellbore, an annulus defined between a wellbore and any tubular arranged within the wellbore, a mud pit, a subterranean formation, etc., combinations thereof, or the like. It should be noted that the term "flow path" does not necessarily imply that a fluid is flowing therein, rather that a fluid is capable of being transported or otherwise flowable therethrough.

As used herein, the term "electromagnetic radiation" refers to radio waves, microwave radiation, infrared and near-infrared radiation, visible light, ultraviolet light, X-ray radiation and gamma ray radiation.

As used herein, the term "optical computing device" refers to an optical device that is configured to receive an input of electromagnetic radiation associated with a fluid and produce an output of electromagnetic radiation from a processing element arranged within the optical computing device. The processing element may be, for example, an integrated computational element (ICE), also known as a multivariate optical element (MOE), used in the optical computing device. The electromagnetic radiation that optically interacts with the processing element is changed so as to be readable by a detector, such that an output of the detector can be correlated to a characteristic of the fluid, such as the type and concentration of a gas in the fluid. The output of electromagnetic radiation from the processing element can be reflected electromagnetic radiation, transmitted electromagnetic radiation, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by the optical computing devices.

As used herein, the term "optically interact" or variations thereof refers to the reflection, transmission, scattering, diffraction, or absorption of electromagnetic radiation either on, through, or from one or more processing elements (i.e., integrated computational elements or multivariate optical elements), a fluid, or a gas present within the fluid. Accordingly, optically interacted light refers to electromagnetic radiation that has been reflected, transmitted, scattered, diffracted, or absorbed by, emitted, or re-radiated, for example, using a processing element, but may also apply to interaction with a fluid or a gas entrained within the fluid.

The exemplary systems and methods described herein will include at least one optical computing device arranged along or in a flow path in order to monitor a fluid contained therein. Each optical computing device may include an electromagnetic radiation source, at least one processing element (e.g., an integrated computational element), and at least one detector arranged to receive optically interacted light from the at least one processing element or the fluid. In some embodiments, the exemplary optical computing devices may be specifically configured for detecting, analyzing, and quantitatively measuring a particular characteristic of the fluid, such as the type and concentration of a gas present within the fluid. In other embodiments, the optical computing devices may be general purpose optical devices, with post-acquisition processing (e.g., through computer means) being used to specifically detect the characteristic of the fluid.

The presently described optical computing devices can perform calculations (analyses) in real-time or near real-time without the need for time-consuming sample processing. Moreover, the optical computing devices can be specifically configured to detect and analyze particular characteristics of a fluid or a gas present within the fluid. As a result, interfering signals are discriminated from those of interest in the fluid by appropriate configuration of the optical computing devices, such that the optical computing devices provide a rapid response regarding the characteristics of the fluid as based on the detected output. In some embodiments, the detected output can be converted into a voltage that is distinctive of the magnitude of the characteristic of the fluid.

The optical computing devices can be configured to detect not only the composition and concentrations of a gas within a fluid, but they also can be configured to determine physical properties and other characteristics of the fluid and/or the gas based on an analysis of the electromagnetic radiation received from the fluid and/or the gas. For example, the optical computing devices can be configured to determine the concentration of an analyte and correlate the determined concentration to a characteristic of the fluid. As will be appreciated, the optical computing devices may be configured to detect as many characteristics (e.g., gas compounds and their respective concentrations) of the fluid as desired. All that is required to accomplish the monitoring of multiple characteristics is the incorporation of suitable processing and detection means within the optical computing device for each characteristic. In some embodiments, the properties of the fluid can be a combination of the properties of the analytes therein (e.g., a linear, non-linear, logarithmic, and/or exponential combination). Accordingly, the more characteristics and analytes that are detected and analyzed using the optical computing devices, the more accurately the properties of the given fluid and/or gas will be determined.

The optical computing devices described herein utilize electromagnetic radiation to perform calculations, as opposed to the hardwired circuits of conventional electronic processors. When electromagnetic radiation interacts with a fluid, unique physical and chemical information about the fluid is encoded in the electromagnetic radiation that is reflected from, transmitted through, or radiated from the fluid. This information is often referred to as the spectral "fingerprint" of the fluid. The optical computing devices described herein are capable of extracting the information of the spectral fingerprint of multiple characteristics or analytes within a fluid, and converting that information into a detectable output relating to one or more characteristics of the fluid or a gas present within the fluid. That is, through suitable configurations of the optical computing devices, electromagnetic radiation associated with a characteristic or analyte of interest of a fluid can be separated from electromagnetic radiation associated with all other components of the fluid in order to estimate the properties of the fluid in real-time or near real-time.

The processing elements used in the exemplary optical computing devices described herein may be characterized as integrated computational elements (ICE). Each ICE is capable of distinguishing electromagnetic radiation related to the characteristic of interest from electromagnetic radiation related to other components of a fluid. Referring to FIG. 1, illustrated is an exemplary ICE 100 suitable for use in the optical computing devices used in the systems and methods described herein. As illustrated, the ICE 100 may include a plurality of alternating layers 102 and 104, such as silicon (Si) and $SiO_2$ (quartz), respectively. In general, these layers 102, 104 consist of materials whose index of refraction is high and low, respectively. Other examples might include niobia and niobium, germanium and germania, MgF, SiO, and other high and low index materials known in the art. The layers 102, 104 may be strategically deposited on an optical substrate 106. In some embodiments, the optical substrate 106 is BK-7 optical glass. In other embodiments, the optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite the optical substrate 106 in FIG. 1), the ICE 100 may include a layer 108 that is generally exposed to the environment of the device or installation. The number of layers 102, 104 and the thickness of each layer 102, 104 are determined from the spectral attributes acquired from a spectroscopic analysis of a characteristic of the fluid using a conventional spectroscopic instrument. The spectrum of interest of a given characteristic typically includes any number of different wavelengths. It should be understood that the exemplary ICE 100 in FIG. 1 does not in fact represent any particular characteristic of a given fluid, but is provided for purposes of illustration only. Consequently, the number of layers 102, 104 and their relative thicknesses, as shown in FIG. 1, bear no correlation to any particular characteristic. Nor are the layers 102, 104 and their relative thicknesses necessarily drawn to scale, and therefore should not be considered limiting of the present disclosure. Moreover, those skilled in the art will readily recognize that the materials that make up each layer 102, 104 (i.e., Si and $SiO_2$) may vary, depending on the application, cost of materials, and/or applicability of the material to the given fluid.

In some embodiments, the material of each layer 102, 104 can be doped or two or more materials can be combined in a manner to achieve the desired optical characteristic. In addition to solids, the exemplary ICE 100 may also contain liquids and/or gases, optionally in combination with solids, in order to produce a desired optical characteristic. In the case of gases and liquids, the ICE 100 can contain a corresponding vessel (not shown), which houses the gases or liquids. Exemplary variations of the ICE 100 may also include holographic optical elements, gratings, piezoelectric, light pipe, digital light pipe (DLP), and/or acousto-optic elements, for example that can create transmission, reflection, and/or absorptive properties of interest.

The multiple layers 102, 104 exhibit different refractive indices. By properly selecting the materials of the layers 102, 104 and their relative thickness and spacing, the ICE 100 may be configured to selectively pass/reflect/refract predetermined fractions of electromagnetic radiation at different wavelengths. Each wavelength is given a predetermined weighting or loading factor. The thickness and spacing of the layers 102, 104 may be determined using a variety of approximation methods from the spectrograph of the characteristic or analyte of interest. These methods may include inverse Fourier transform (IFT) of the optical transmission spectrum and structuring the ICE 100 as the physical representation of the IFT. The approximations convert the IFT into a structure based on known materials with constant refractive indices.

The weightings that the layers 102, 104 of the ICE 100 apply at each wavelength are set to the regression weightings described with respect to a known equation, or data, or spectral signature. Briefly, the ICE 100 may be configured to perform the dot product of the input light beam into the ICE 100 and a desired loaded regression vector represented by each layer 102, 104 for each wavelength. As a result, the output light intensity of the ICE 100 is related to the characteristic or analyte of interest.

Figure 2:
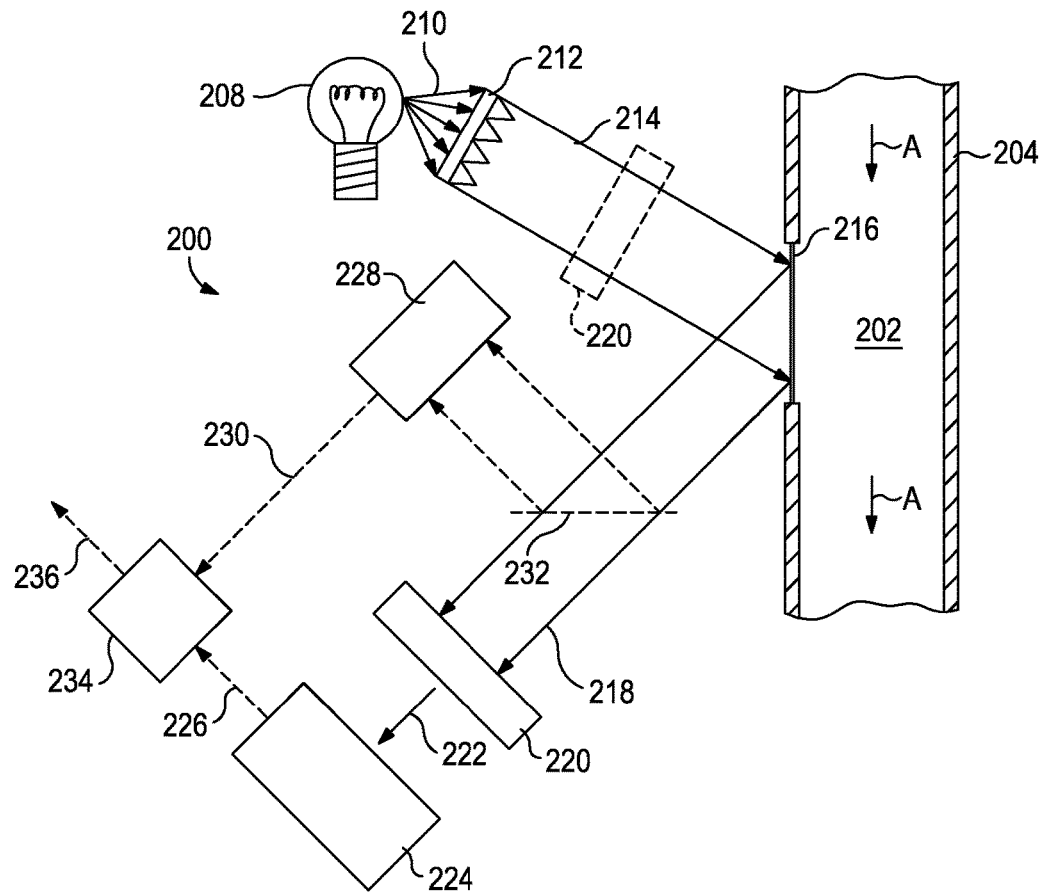
FIG. 2 illustrates an exemplary optical computing device for monitoring a fluid, according to one or more embodiments.

Referring now to FIG. 2, illustrated is an exemplary optical computing device 200 for monitoring a fluid 202, according to one or more embodiments. In the illustrated embodiment, the fluid 202 may be contained or otherwise flowing within an exemplary flow path 204. The flow path 204 may be a flow line, a pipeline, a wellbore, an annulus defined within a wellbore, or any flow lines or pipelines extending to/from a wellbore. The fluid 202 present within the flow path 204 may be flowing in the general direction indicated by the arrows A (i.e., from upstream to downstream). Portions of the flow path 204 may be arranged substantially vertical, substantially horizontal, or any directional configuration therebetween, without departing from the scope of the disclosure.

The optical computing device 200 may be configured to determine a characteristic of interest in the fluid 202, such as the type and/or concentration of a gas present within the fluid 202. In some embodiments, the device 200 may include an electromagnetic radiation source 208 configured to emit or otherwise generate electromagnetic radiation 210. The electromagnetic radiation source 208 may be any device capable of emitting or generating electromagnetic radiation, as defined herein. For example, the electromagnetic radiation source 208 may be a light bulb, a light emitting diode (LED), a laser, a blackbody, a photonic crystal, an X-Ray source, combinations thereof, or the like. In some embodiments, a lens 212 may be configured to collect or otherwise receive the electromagnetic radiation 210 and direct a beam 214 of electromagnetic radiation 210 toward the fluid 202. The lens 212 may be any type of optical device configured to transmit or otherwise convey the electromagnetic radiation 210 as desired, such as a normal lens, a Fresnel lens, a diffractive optical element, a holographic graphical element, a mirror (e.g., a focusing mirror), or a type of collimator. In other embodiments, the lens 212 may be omitted from the device 200 and the electromagnetic radiation 210 may instead be directed toward the fluid 202 directly from the electromagnetic radiation source 208.

In one or more embodiments, the device 200 may also include a sampling window 216 arranged adjacent to or otherwise in contact with the fluid 202 for detection purposes. The sampling window 216 may be made from a variety of transparent, rigid or semi-rigid materials that are configured to allow transmission of the electromagnetic radiation 210 therethrough. For example, the sampling window 216 may be made of, but is not limited to, glasses, plastics, semi-conductors, crystalline materials, polycrystalline materials, hot or cold-pressed powders, combinations thereof, or the like. After passing through the sampling window 216, the electromagnetic radiation 210 impinges upon and optically interacts with the fluid 202. As a result, optically interacted radiation 218 is generated by and reflected from the fluid 202. Those skilled in the art, however, will readily recognize that alternative variations of the device 200 may allow the optically interacted radiation 218 to be generated by being transmitted, scattered, diffracted, absorbed, emitted, or re-radiated by and/or from the fluid 202, without departing from the scope of the disclosure.

The optically interacted radiation 218 generated by the interaction with the fluid 202 may be directed to or otherwise be received by an ICE 220 arranged within the device 200. The ICE 220 may be a spectral component substantially similar to the ICE 100 described above with reference to FIG. 1. Accordingly, in operation the ICE 220 may be configured to receive the optically interacted radiation 218 and produce modified electromagnetic radiation 222 corresponding to a particular characteristic of the fluid 202. In particular, the modified electromagnetic radiation 222 is electromagnetic radiation that has optically interacted with the ICE 220, whereby an approximation of the regression vector corresponding to the characteristic of the fluid 202 is obtained.

While FIG. 2 depicts the ICE 220 as receiving reflected electromagnetic radiation from the fluid 202, the ICE 220 may be arranged at any point along the optical train of the device 200, without departing from the scope of the disclosure. For example, in one or more embodiments, the ICE 220 (as shown in dashed lines) may be arranged within the optical train prior to the sampling window 216 and equally obtain substantially the same results. In other embodiments, the ICE 220 may generate the modified electromagnetic radiation 222 through reflection, instead of transmission therethrough.

Moreover, while only one ICE 220 is shown in the device 200, embodiments are contemplated herein which include the use of at least two ICE components in the device 200 configured to cooperatively determine the characteristic of interest in the fluid 202. For example, two or more ICE may be arranged in series or parallel within the device 200 and configured to receive the optically interacted radiation 218 and thereby enhance sensitivities and detector limits of the device 200. In other embodiments, two or more ICE may be arranged on a movable assembly, such as a rotating disc or an oscillating linear array, which moves such that individual ICE components are able to be exposed to or otherwise optically interact with electromagnetic radiation for a distinct brief period of time. The two or more ICE components in any of these embodiments may be configured to be either associated or disassociated with the characteristic of interest in the fluid 202. In other embodiments, the two or more ICE may be configured to be positively or negatively correlated with the characteristic of interest in the fluid 202.

In some embodiments, it may be desirable to monitor more than one characteristic of interest at a time using the device 200, such as detecting multiple types or compounds of gases within the fluid 202. In such embodiments, various configurations for multiple ICE components can be used, where each ICE component is configured to detect a particular and/or distinct characteristic of interest. In some embodiments, the characteristic can be analyzed sequentially using multiple ICE components that are provided a single beam of electromagnetic radiation being reflected from or transmitted through the fluid 202. In some embodiments, multiple ICE components can be arranged on a rotating disc, where the individual ICE components are only exposed to the beam of electromagnetic radiation for a short time. Advantages of this approach can include the ability to analyze multiple characteristics of the fluid 202 using a single optical computing device 200 and the opportunity to assay additional characteristics (e.g., types or compounds of gases within the fluid 202) simply by adding additional ICE components to the rotating disc.

In other embodiments, multiple optical computing devices can be placed at a single location along the flow path 204, where each optical computing device contains a unique ICE that is configured to detect a particular characteristic of interest in the fluid 202. In such embodiments, a beam splitter can divert a portion of the electromagnetic radiation being reflected by, emitted from, or transmitted through the fluid 202 and into each optical computing device. Each optical computing device, in turn, can be coupled to a corresponding detector or detector array that is configured to detect and analyze an output of electromagnetic radiation from the respective optical computing device. Parallel configurations of optical computing devices can be particularly beneficial for applications that require low power inputs and/or no moving parts.

Those skilled in the art will appreciate that any of the foregoing configurations can further be used in combination with a series configuration in any of the present embodiments. For example, two optical computing devices having a rotating disc with a plurality of ICE components arranged thereon can be placed in series for performing an analysis at a single location along the length of the flow path 204. Likewise, multiple detection stations, each containing optical computing devices in parallel, can be placed in series for performing a similar analysis.

The modified electromagnetic radiation 222 generated by the ICE 220 may subsequently be conveyed to a detector 224 for quantification of the signal. The detector 224 may be any device capable of detecting electromagnetic radiation, and may be generally characterized as an optical transducer. In some embodiments, the detector 224 may be, but is not limited to, a thermal detector such as a thermopile or photoacoustic detector, a semiconductor detector, a piezoelectric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 224 may be configured to produce an output signal 226 in real-time or near real-time in the form of a voltage (or current) that corresponds to the particular characteristic of interest in the fluid 202. The voltage returned by the detector 224 is essentially the dot product of the optical interaction of the optically interacted radiation 218 with the respective ICE 220 as a function of the concentration of the characteristic of interest of the fluid 202. As such, the output signal 226 produced by the detector 224 and the concentration of the characteristic may be related, for example, directly proportional. In other embodiments, however, the relationship may correspond to a polynomial function, an exponential function, a logarithmic function, and/or a combination thereof.

In some embodiments, the device 200 may include a second detector 228, which may be similar to the first detector 224 in that it may be any device capable of detecting electromagnetic radiation. The second detector 228 may be used to detect radiating deviations stemming from the electromagnetic radiation source 208. Undesirable radiating deviations can occur in the intensity of the electromagnetic radiation 210 due to a wide variety of reasons and potentially causing various negative effects on the device 200. These negative effects can be particularly detrimental for measurements taken over a period of time. In some embodiments, radiating deviations can occur as a result of a build-up of film or material on the sampling window 216 which has the effect of reducing the amount and quality of light ultimately reaching the first detector 224. Without proper compensation, such radiating deviations could result in false readings and the output signal 226 would no longer be primarily or accurately related to the characteristic of interest.

To compensate for these types of undesirable effects, the second detector 228 may be configured to generate a compensating signal 230 generally indicative of the radiating deviations of the electromagnetic radiation source 208, and thereby normalize the output signal 226 generated by the first detector 224. As illustrated, the second detector 228 may be configured to receive a portion of the optically interacted radiation 218 via a beamsplitter 232 in order to detect the radiating deviations. In other embodiments, however, the second detector 228 may be arranged to receive electromagnetic radiation from any portion of the optical train in the device 200 in order to detect the radiating deviations, without departing from the scope of the disclosure.

In some applications, the output signal 226 and the compensating signal 230 may be conveyed to or otherwise received by a signal processor 234 communicably coupled to both the detectors 224, 228. The signal processor 234 may be a computer including a processor and a machine-readable storage medium having instructions stored thereon, which, when executed by the processor 234, cause the optical computing device 200 to perform a number of operations, such as determining a characteristic of interest of the fluid 202. For instance, the concentration of each characteristic detected with the optical computing device 200 can be fed into an algorithm operated by the signal processor 234. The algorithm can be part of an artificial neural network configured to use the concentration of each detected characteristic in order to evaluate the overall characteristic(s) or quality of the fluid 202.

The signal processor 234 may also be configured to computationally combine the compensating signal 230 with the output signal 226 in order to normalize the output signal 226 in view of any radiating deviations detected by the second detector 228. Computationally combining the output and compensating signals 226, 230 may entail computing a ratio of the two signals 226, 230. For example, the concentration or magnitude of each characteristic determined using the optical computing device 200 can be fed into an algorithm run by the signal processor 234. The algorithm may be configured to make predictions on how the characteristics of the fluid 202 change if the concentrations of one or more components or additives are changed relative to one another.

In real-time or near real-time, the signal processor 234 may be configured to provide a resulting output signal 236 corresponding to the characteristic of interest in the fluid 202, such as the concentration of a gas present in the fluid 202. The resulting output signal 236 may be readable by an operator who can consider the results and make proper adjustments or take appropriate action, if needed. In some embodiments, the resulting signal output 236 may be conveyed, either wired or wirelessly, to an operator for consideration. In other embodiments, the resulting output signal 236 may be recognized by the signal processor 234 as being within or without a predetermined or preprogrammed range of suitable operation and may alert the operator of an out of range reading so appropriate corrective action may be taken, or otherwise autonomously undertake the appropriate corrective action such that the resulting output signal 236 returns to a value within the predetermined or preprogrammed range of suitable operation.

Figure 3:
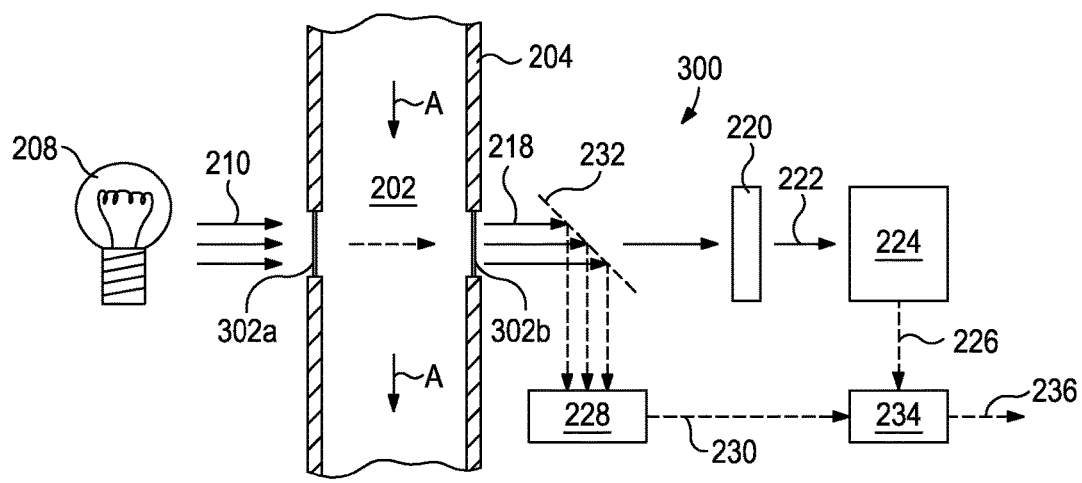
FIG. 3 illustrates another exemplary optical computing device for monitoring a fluid, according to one or more embodiments.

Referring now to FIG. 3, illustrated is another exemplary optical computing device 300 for monitoring the fluid 202, according to one or more embodiments. The optical computing device 300 may be similar in some respects to the optical computing device 200 of FIG. 2, and therefore may be best understood with reference thereto where like numerals indicate like elements that will not be described again. Again, the optical computing device 300 may be configured to determine the concentration of a characteristic of interest in the fluid 202, such as the concentration of a gas within the fluid 202, as contained within the flow path 204. Unlike the device 200 of FIG. 2, however, the optical computing device 300 in FIG. 3 may be configured to transmit the electromagnetic radiation 210 through the fluid 202 via a first sampling window 302a and a second sampling window 302b arranged radially-opposite the first sampling window 302a on the flow path 204. The first and second sampling windows 302a,b may be similar to the sampling window 216 described above in FIG. 2 and therefore will not be described again.

As the electromagnetic radiation 210 passes through the fluid 202 via the first and second sampling windows 302a,b, it optically interacts with the fluid 202 and optically interacted radiation 218 is subsequently directed to or otherwise received by the ICE 220 as arranged within the device 300. It is again noted that, while FIG. 3 depicts the ICE 220 as receiving the optically interacted radiation 218 as transmitted through the sampling windows 302a,b, the ICE 220 may equally be arranged at any point along the optical train of the device 300, without departing from the scope of the disclosure. For example, in one or more embodiments, the ICE 220 may be arranged within the optical train prior to the first sampling window 302a and equally obtain substantially the same results. In yet other embodiments, the ICE 220 may generate the modified electromagnetic radiation 222 through reflection, instead of transmission therethrough. Moreover, as with the device 200 of FIG. 2, embodiments are contemplated herein which include the use of at least two ICE components in the device 300 configured to cooperatively determine the characteristic of interest in the fluid 202.

The modified electromagnetic radiation 222 generated by the ICE 220 is subsequently conveyed to the detector 224 for quantification of the signal and generation of the output signal 226 which corresponds to the particular characteristic of interest in the fluid 202. The device 300 may also include the second detector 228 for detecting radiating deviations stemming from the electromagnetic radiation source 208. As illustrated, the second detector 228 may be configured to receive a portion of the optically interacted radiation 218 via the beamsplitter 232 in order to detect the radiating deviations. The output signal 226 and the compensating signal 230 may then be conveyed to or otherwise received by the signal processor 234 which may computationally combine the two signals 230, 226 and provide in real-time or near real-time the resulting output signal 236 corresponding to the concentration of the characteristic of interest in the fluid 202.

Those skilled in the art will readily appreciate the various and numerous applications that the optical computing devices 200, 300, and various alternative configurations thereof, may be suitably used with.

The systems and methods described herein utilize at least one optical computing device in combination with at least one gas analysis device to more accurately measure the gas composition in the drilling fluid at various points in a drilling fluid circulation system. The gas analysis devices measure the concentrations of all the gases of interest in the gas extracted from the drilling fluid, and the optical computing devices measure the concentration of only some of the gases of interest. A correction factor can be derived from a comparison of the measurements of the two types of devices. Depending on the configuration of the system, the correction factor can be a single point correction factor, a dual point correction factor, or a point-to-point correction factor.

Figure 4:
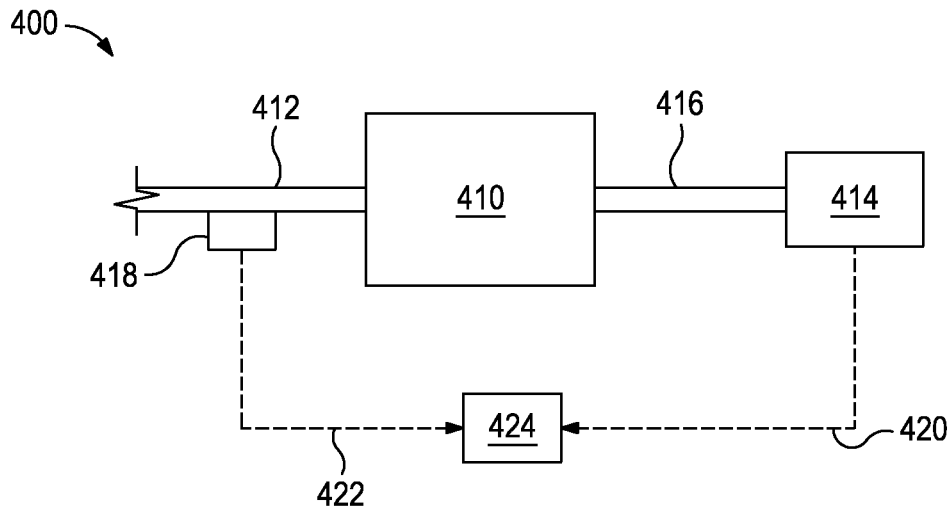
FIG. 4 illustrates an exemplary wellbore drilling assembly that may employ one or more optical computing devices for monitoring a fluid, according to one or more embodiments.

FIG. 4 provides an illustrative representation of a portion of a system 400 suitable for deriving a single point correction factor for the gas composition of a fluid. The fluid flows into a degasser 410 through feed line 412. The degasser 410 extracts at least a portion of the gas entrained in the fluid. At least a portion of the extracted gas may then be transferred to at least one gas analysis device 414 via feed line 416. The gas analysis devices 414 may analyze the composition of the extracted gas for the concentration of gases of interest and the amount of total gas. At least one optical computing device 418 may be arranged in the system 400 before the degasser 410 and be configured to measure the concentration of a reference compound and a gas from the formation (e.g., methane or ethane). The reference compound may be a volatile compound that is introduced into the fluid (e.g., fluorinated hydrocarbons), indigenous to the fluid (e.g., $CO_2$), or a spectral overlapping gas (e.g., ethane that overlaps with methane or ethane that overlaps ethane). Each of the gas analysis devices 414 and optical computing devices 418 may produce output signals 420,422, respectively, corresponding to the measurements taken. The output signals 420,422 are received by a signal processor 424 communicably coupled to the gas analysis devices 414 and optical computing devices 418.

The signal processor 424 may be similar to the signal processor 234 of FIGS. 2 and 3 and may be configured to receive and process the output signals 420,422. In particular, the signal processor 424 may employ an algorithm configured to calculate or otherwise determine the concentration of the gases detected by the gas analysis devices 414, calculate a correction factor, apply the correction factor to the output signals 422 of the optical computing devices 418 to calculate the concentration of the gas detected by the optical computing devices 418, and extrapolate the concentration of all the gases of interest in the drilling fluid.

For example, the optical computing devices 418 may be configured to measure the concentration of methane in the drilling fluid ("$[CH_4]_{DF}$") and the concentration of the reference compound in the drilling fluid ("$[ref]_{DF}$"). The gas analysis devices 414 may be configured to measure the concentration of methane in the extracted gas ("$[CH_4]_{EG}$"), the concentration of the reference compound in the extracted gas ("$[ref]_{EG}$"), and the concentration of one or more other gases of interest in the extracted gas ("$[gas]_{EG}$"). A single point correction factor can be determined by comparing $[CH_4]_{DF}/[CH_4]_{EG}$ and $[ref]_{DF}/[ref]_{EG}$ or variations in $[CH_4]_{DF}/[CH_4]_{EG}$ and $[ref]_{DF}/[ref]_{EG}$. The comparison of the concentrations in the drilling fluid and extracted gas may include sums or other methods to account for interaction factors from other compounds. When the spectral response of the reference gas has peaks within a spectral response of an overlapping gas, peak fittings can be used to determine overlap at the point of measurement. The intensity of overlap then be removed before determining the correction factor. After the correction factor has been determined, curve fitting can be used to apply the correction factor to each of the $[gas]_{EG}$ and extrapolate the concentration of all the gases of interest in the drilling fluid.

Figure 5:
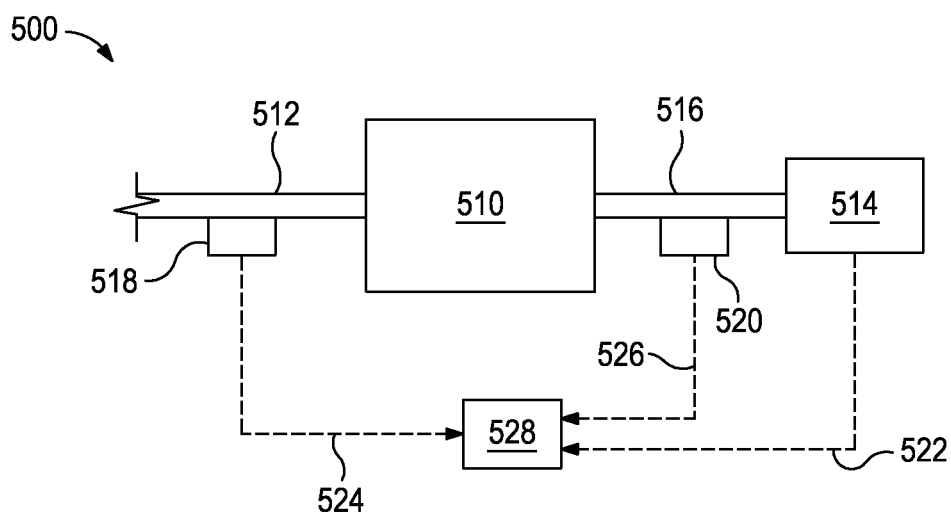
FIG. 5 provides an illustrative representation of a portion of a system suitable for deriving a dual point correction factor for the gas composition of a fluid, according to one or more embodiments.

FIG. 5 provides an illustrative representation of a portion of a system 500 suitable for deriving a dual point correction factor for the gas composition of a fluid. The fluid flows into a degasser 510 through feed line 512. The degasser 510 extracts at least a portion of the gas entrained in the fluid. At least a portion of the extracted gas may then be transferred to at least one gas analysis device 514 via feed line 516. The gas analysis devices 514 may analyze the composition of the extracted gas for the concentration of gases of interest and the amount of total gas. At least one optical computing device 518 may be arranged in the system 500 before the degasser 510 and be configured to measure the concentration of a reference compound and a gas from the formation. At least one optical computing device 520 may be arranged in the system 500 between the degasser 510 and the gas analysis devices 514 and be configured to measure the concentration of the reference compound and the gas from the formation. Each of the gas analysis devices 514 and optical computing devices 518,520 may produce output signals 522,524,526, respectively, corresponding to the measurements taken. The output signals 522,524,526 are received by a signal processor 528 communicably coupled to the gas analysis devices 514 and optical computing devices 518,520.

A dual point calibration may advantageously be able to correct for a non-linear background in measurements, which may be contributed to by a compound with an overlapping spectrum.

In some instances, the foregoing calibration methods may utilize more than one reference compound. In some instances, no reference gas may be used by developing a direct relationship between and calibration curve for the measurements of the optical computing devices and the gas analysis devices, which may be referred to herein as a point-to-point calibration.

In any of the foregoing calibration arrangements and methods, the calibration may be performed continuously in some embodiments. Alternatively, in some instance, the calibration may be performed periodically (e.g., once every 15 minutes, once every hour, etc.). Additionally, the calibration may, in some instance, be performed on-demand (e.g., as triggered by an operator). This further contributes to the accuracy of the systems and methods described herein for measuring gas content and gas composition in a drilling fluid in real-time.

In the illustrated examples of the calibrations, the optical computing devices are deployed proximal to the degasser. However, additional optical computing devices can be deployed at various points within a drilling fluid circulation system to monitor the drilling fluid and its associated gas content using the calibrations for each type of optical computing device being determined with one of the above or similar systems/methods. Depending on the location of the particular optical computing device, different types of information about the fluid can be obtained. In some cases, for example, the optical computing devices can be used to monitor the type and concentration of gases therein before and after the drilling fluid circulates into and out of a wellbore. In other cases, the optical computing devices may be used to analyze an extracted gas sample in real-time following its extraction from the drilling fluid via a traditional drilling fluid sampling process. In other cases, the optical computing devices may be used to monitor the drilling fluid at or near a wellbore choking device so as to register real-time gas concentrations of the drilling fluid while the drilling fluid circulates at wellbore conditions.

Figure 6:
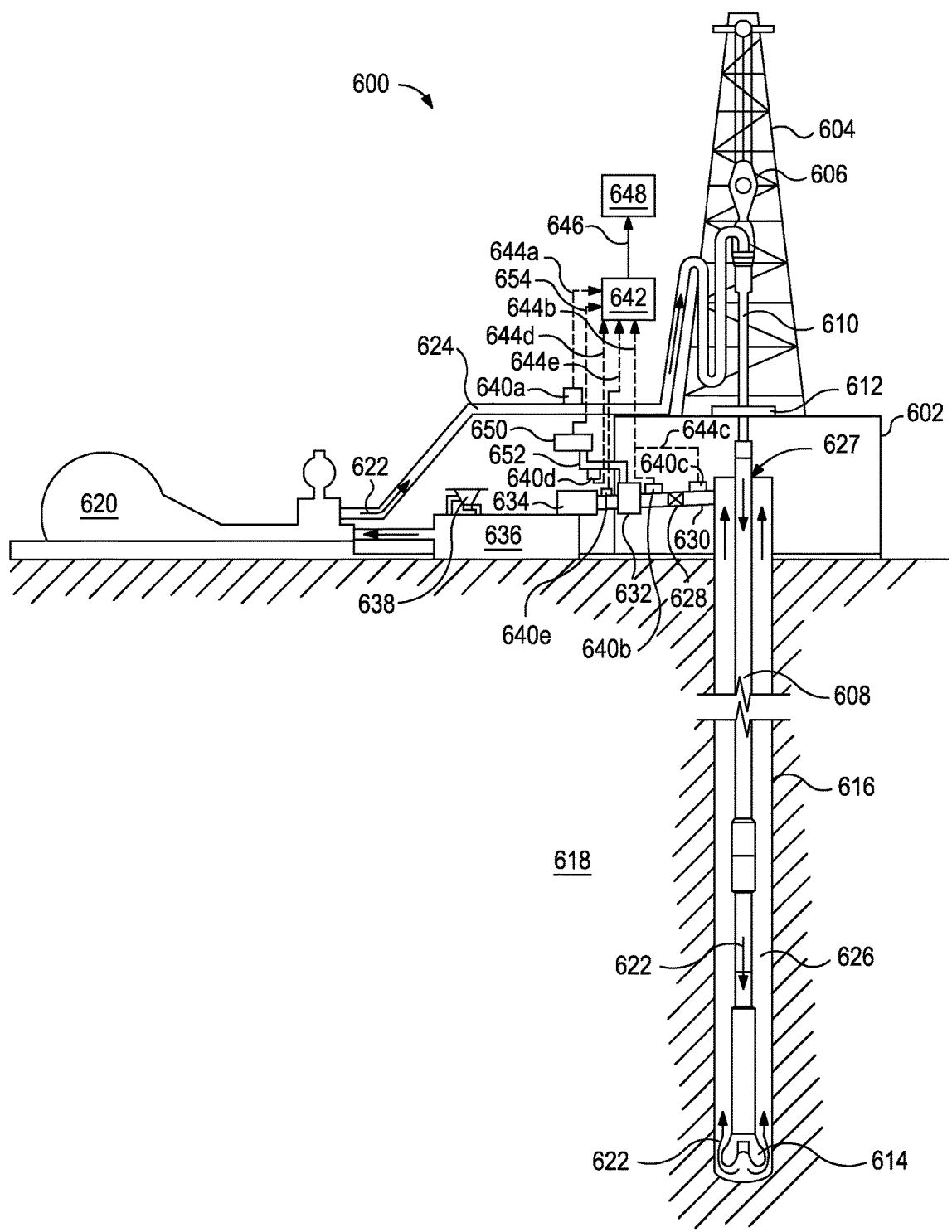
FIG. 6 illustrates an exemplary wellbore drilling assembly that with optical computing devices in order to monitor a drilling fluid or a completion fluid, according to one or more embodiments.

For example, referring now to FIG. 6, illustrated is an exemplary wellbore drilling assembly 600 that may employ one or more optical computing devices as described herein in order to monitor a drilling fluid or a completion fluid, according to one or more embodiments. The drilling assembly 600 may include a drilling platform 602 that supports a derrick 604 having a traveling block 606 for raising and lowering a drill string 608. A kelly 610 supports the drill string 608 as it is lowered through a rotary table 612. A drill bit 614 is attached to the distal end of the drill string 608 and is driven either by a downhole motor and/or via rotation of the drill string 608 from the well surface. As the bit 614 rotates, it creates a borehole 616 that penetrates various subterranean formations 618.

A pump 620 (e.g., a mud pump) circulates drilling fluid 622 through a feed pipe 624 and to the kelly 610, which conveys the drilling fluid 622 downhole through an interior conduit defined in the drill string 608 and through one or more orifices in the drill bit 614. The drilling fluid 622 is then circulated back to the surface via an annulus 626 defined between the drill string 608 and the walls of the borehole 616. The drilling fluid 622 provides hydrostatic pressure to prevent formation fluids from entering into the borehole 616 and keeps the drill bit 614 cool and clean during drilling. The drilling fluid 622 also serves to carry drill cuttings and solids out of the borehole 616 and suspend the drill cuttings and solids while drilling is paused and/or when the drill bit 614 is brought in and out of the borehole 616.

As the spent drilling fluid 622 returns to the surface, it may exit the annulus 626 at the wellhead 627 and subsequently pass through one or more chokes or choke valves 628 (one shown) via an interconnecting flow line 630. The choke valve 628 may be used to maintain or otherwise regulate the pressure on the annulus 626 at surface, for example in the range of about 100 psi to about 1500 psi. As a result, this will enable drilling to continue underbalanced and is useful in reducing formation damage, but also to facilitate increases in drilling speed. It will be appreciated, however, that the choke valve(s) 628 may be omitted in other embodiments and the spent drilling fluid 622 may instead return to the surface at atmospheric pressures, without departing from the scope of the disclosure.

Following the choke valve 628, the spent drilling fluid 622 may be conveyed to one or more drilling fluid rehabilitation devices via the interconnecting flow line 630. Such drilling fluid rehabilitation devices may include, but are not limited to, one or more degassing units 632 and solids control equipment 634 (e.g., shakers). The degassing unit 632 may be any device or machine configured to separate from the drilling fluid 622 gases (i.e., hydrocarbon and non-hydrocarbon gas species) that may have been entrained in the drilling fluid 622 while circulating in and out of the borehole 616. The solids control equipment 634 may be configured to substantially remove the drill cuttings and solids from the drilling fluid 622 and deposit a "cleaned" drilling fluid 622 into a nearby retention pit 636 (i.e., a mud pit).

Several additives or components may be added to the drilling fluid 622 in order to maintain the drilling fluid 622 in proper working order and otherwise enhance drilling capabilities. In some embodiments, the additives and components may be added to the drilling fluid 622 via a mixing hopper 638 fluidly coupled to the retention pit 636. Exemplary components that may be added to the drilling fluid 622 include, but are not limited to, emulsions, weighting materials, viscosifiers, thickeners, rheology modifiers, thinners, deflocculants, anionic polyelectrolytes (e.g., acrylates, polyphosphates, lignosulfonates, tannic acid derivates, etc.), high-heat polymers, clay stabilizers, clay inhibitors, tar treatments, water and other base fluids, combinations thereof, and the like. The rehabilitated drilling fluid 622 may then be recirculated and pumped back into the borehole 616 with the pump 620 via the feed pipe 624.

According to the present disclosure, mud logging gas analysis of the drilling fluid 622 may be undertaken using optical computing devices 640 and gas analysis devices 650 with calibrations of the optical computing devices 640 according to the methods and configurations described relative to FIGS. 4-5 or similar thereto. The gas analysis device 650 received gas from the degassing unit 632 through flow line 652. Depending on the analysis method, optical computing devices may be arranged in various locations throughout the circulation system of the drilling assembly 600. For example, as shown in FIG. 6, optical computing devices 640a, 640b, 640c, 640d, and 640e may be arranged along flow pipe 624, along flow line 630 between the choke valve 628 and the degassing unit 632, along flow line 630 before choke valve 628, along the flow line 652 between the degassing unit 632 and the gas analysis devices 650, and along flow line 630 between the degassing unit 632 and the solids control equipment 634, respectively. The optical computing devices 640a-e may be substantially similar to at least one of the optical computing devices 200, 300 of FIGS. 2 and 3, respectively, and therefore will not be described again in detail. In exemplary operation, the optical computing devices 640a-e may be configured to measure and report real-time characteristics of the drilling fluid 622, such as the type and/or concentration of one or more gases present therein at their respective monitoring locations.

In one or more embodiments, the optical computing devices 640a-e may be communicably coupled to a signal processor 642 and configured to convey corresponding output signals 644a-e, respectively, to the signal processor 642. The signal processor 642 may be similar to the signal processor 234 of FIGS. 2 and 3 and may be configured to receive and process the output signals 644a-e. In particular, the signal processor 642 may employ an algorithm configured to calculate or otherwise determine the concentration or type of a gas detected at each monitoring location. The signal processor 642 may further be configured to determine the differences between any two or more of the output signals 644a-e. In other words, the signal processor 642 may be configured to determine how the concentration of the gas and/or the magnitude of the characteristic of interest in the fluid 622 changed between each monitoring location.

Further, the signal processor 642 may be configured receive output signals 654 from the gas analysis devices 650, so as to perform a comparative analysis between the gas concentrations measured by the gas analysis devices 650 and individual optical computing devices 640a-e (described further herein). In real-time or near real-time, the signal processor 642 may be configured to provide a resulting output signal 646 corresponding to the concentration of individual gases or the total gas, each of which may be measured or derived as described further herein.

In some embodiments, the resulting output signal 646 may be conveyed, either wired or wirelessly, to one or more peripheral devices 648 communicably coupled to the signal processor 642. The peripheral devices 648 may include, but are not limited to, a mobile device, computer monitor, or a printer coupled to a computer. In some embodiments, the peripheral devices 648 may be configured to provide one or more graphical outputs such as a Pixler plot, a Haworth Plot, or a gas-ratio plot, depicting various properties, parameters, and characteristic(s) detected in the fluid 622 (e.g., the concentration of individual gases or the total gas in the drilling fluid). A well operator may then be able to consult and interpret the graphical output and thereby make intelligent decisions on how best to manage the well in response thereto.

In other embodiments, the peripheral devices 648 may include an audible or visual alarm mechanism or device that may be triggered. For example, the one or more of the output signals 644a-e, 654 or an analysis thereof may be recognized by the signal processor 642 as being within or without a predetermined or preprogrammed range of suitable operation for the drilling fluid 622. If the output signals 644a-e, 654 or an analysis thereof exceed the predetermined or preprogrammed range of operation, the resulting output signal 646 may trigger an alarm forming part of the peripheral device 648 and the alarm may be configured to alert the operator so appropriate corrective action may be taken on the drilling fluid 622. In some embodiments, the signal processor 642 may be configured to autonomously undertake the appropriate corrective action such that the resulting output signal 646 returns to a value within the predetermined or preprogrammed range of suitable operation. For example, the signal processor 642 may be communicably coupled to an automated control system (not shown) that may be configured to undertake the required corrective action.

As illustrated, optical computing device 640b and gas analysis device 650 may be configured and operate similar to that of optical computing device 418 and gas analysis device 415 of FIG. 4 to provide a single-point calibration that may be applied to other optical computing devices arranged in the system 600. Further, optical computing devices 640b, 640d and gas analysis device 650 may be configured and operate similar to that of optical computing devices 518, 520 and gas analysis device 514 of FIG. 5 to provide a dual-point calibration that may be applied to other optical computing devices arranged in the system 600.

In some embodiments, gas concentration measured from the optical computing device 640e arranged along the flow line 630 after the degasser 632 may be compared to the gas concentration from the optical computing device 640b arranged before the degasser to provide a degassing efficiency.

In some embodiments, a first optical computing device 640a may be arranged to monitor the drilling fluid 622 as it is being introduced into the borehole 616 and a second optical computing device 640b may be arranged to monitor the drilling fluid 622 after it has returned to the surface and is otherwise de-pressurized via the choke valve 628. More particularly, the first optical computing device 640a may be arranged in the feed pipe 624 leading to the derrick 604 from the pump 620 (or otherwise at any fluidly communicable location following the pump 620 and before the borehole 616), and the second optical computing device 640b may be arranged on or otherwise coupled to the flow line 630 before the degassing unit 632 (e.g., adjacent an inlet to the degassing unit 632). As will be appreciated, more than one optical computing device may be arranged at each of these monitoring locations, without departing from the scope of the disclosure.

The first output signal 644a may be indicative of the type/concentration of a gas in the drilling fluid 622 or another characteristic of the fluid 622 as the drilling fluid 622 enters the borehole 616. Likewise, the second output signal 644b may be indicative of the type/concentration of the gas or another characteristic of the fluid 622 as the drilling fluid 622 exits the borehole 616 de-pressurized. The signal processor 642 may receive the output signals 644a,b in real-time and provide the resulting output signal 646 that may be considered by an operator via the one or more peripheral devices 648, as described above. In some embodiments, the resulting output signal 646 may inform the operator of the type/concentration of gas in the drilling fluid 622 as the drilling fluid 622 enters the borehole 616, as per the first output signal 644a. In other embodiments, the resulting output signal 646 may inform the operator of the type/concentration of the gas in the drilling fluid 622 as the drilling fluid 622 exits the borehole 616, as per the second output signal 644b. As a result, the operator may be able to conduct mud logging gas analyses of the drilling fluid 622 without having to extract a gas sample from the returning drilling fluid 622.

In yet other embodiments, the signal processor 642 may be configured to make a comparison between the first and second output signals 644a,b, and thereby provide the operator with a resulting output signal 646 via the peripheral devices 648 that details the differences between the two output signals 644a,b. As such, the operator may be apprised as to the quantity and concentration of one or more gases that may have entered or otherwise become entrained in the drilling fluid 622 while circulating through the borehole 616. Such data may be useful in providing information as to the hydrocarbon content of the rock being drilled through and, as a result, the operator may decide to adjust one or more drilling or completion parameters in response thereto.

For example, in some embodiments, the resulting output signal 646 may inform the operator that a particular type or quantity of favorable gas is found in a particular strata or region of the subterranean formation 618 while drilling. As a result, at least one drilling parameter may be adjusted in response thereto, such as altering the geosteering of the drill bit 614 so that the borehole 616 may be drilled or formed substantially in that strata or zone. In some embodiments, the favorable gas may be one or more hydrocarbons that may be produced for processing. In other embodiments, however, the favorable gas may be helium. Those skilled in the art will readily recognize that an increased amount of helium returning to the surface as entrained in the drilling fluid 622 may be an indication of high porosity in the formation 618, and high porosity can signify a zone capable of increased production rates. When such gases and hydrocarbons are detected, the operator may alter the geosteering well path such that the borehole remains substantially in that stratum, thereby maximizing potential hydrocarbon production and efficiencies.

As will be appreciated, this may prove especially advantageous in deviated or horizontal wells where altering the geosteering may have the effect of maintaining the well path substantially parallel and otherwise within a hydrocarbon-bearing stratum or region. This may also prove advantageous, however, in vertical wells where the well operator may be able to log the area of the vertical borehole 616 where a high gas content is detected. At a later time, the operator may choose to return to that location and complete the borehole 616 at that location such that the hydrocarbons residing in the formation 618 at that location may be effectively produced with greater efficiency. Accordingly, the well completion design may be optimized in response to resulting output signal 646 and what is provided via the peripheral devices 648. Some well completion designs that may be altered include, but are not limited to, changing a cementing program, changing a casing program or design, or optimizing placement of downhole perforations, sliding sleeves, and slotted liners. Optimizations resulting from such well completion alterations may include containment of unwanted fluids downhole, such as water or unwanted gas, and may also include optimizing isolation of zones from which production is not required. Further, nearby wells having similar (correlated) output signals 644a-c or output signal 646 may implement similar optimizations.

In some embodiments, the resulting output signal 646 may also be configured to inform an operator via the peripheral devices 648 of hazardous, corrosive, or otherwise toxic gases that may be entrained in the drilling fluid 622. Hazardous, corrosive, and/or toxic gases, such as hydrogen sulfide ($H_2S$) and the like, may pose a danger to rig operators and the surrounding environment. In at least one embodiment, for example, the second output signal 644b of the second optical computing device 640b may provide the real-time concentration of hydrogen sulfide ($H_2S$) entrained in the drilling fluid 622 as it returns to the surface. If the registered level of $H_2S$ surpasses a predetermined "safe" limit, the signal processor 642 may be configured to trigger an alarm by sending the resulting output signal 646 to the peripheral devices 648 indicating the same. In response to the alarm, the operator may act by shutting down the well or adding $H_2S$ scavengers or other additives to the drilling fluid 622 via the hopper 638 to remedy the situation.

In some embodiments, the hazardous, corrosive, or otherwise toxic gas may be methane as entrained in the drilling fluid 622. Since methane is highly explosive, increased amounts of the gas in the returning drilling fluid 622 may pose a substantial risk to rig operators and the surrounding environment. Accordingly, if there is an excessive amount of methane being detected by, for example, the second optical computing device 640b, such that it surpasses a predetermined "safe" limit, the signal processor 642 may be configured to trigger an alarm via the resulting output signal 646 and the peripheral devices 648. In response to the alarm, the operator may act to remedy the situation. For example, the operator may "shut in" the well using blow-out preventers or the like and then extract the methane in a controlled manner using choke and kill lines associated with the blow-out preventers.

In some embodiments, the drilling fluid 622 returned to the surface may be monitored using the third optical computing device 640c prior to full de-pressurization. As illustrated, the third optical computing device 640c may be arranged in fluid communication with the interconnecting flow line 630 following the wellhead 627 and otherwise arranged prior to the choke valve 628. Similar to the second optical computing device 640b, the third optical computing device 640c may be configured to monitor the drilling fluid 622 after its return to the surface for gases (both hydrocarbon and non-hydrocarbon gas species) that may have become entrained therein after having circulated through the borehole 616. When the drilling fluid 622 exits the choke valve 628, any gases entrained therein will immediately break out or otherwise precipitate out of the drilling fluid 622. Accordingly, the third optical computing device 640c may be advantageous in providing a real or near real-time concentration of one or more gases in the drilling fluid 622 as it circulates at or near actual downhole drilling environment conditions. The output signal 644c from the third optical computing device 640c, therefore, may be useful in mud logging gas analysis of the drilling fluid 622 at downhole operating conditions.

Similar to the second optical computing device 640b, the third optical computing device 640c may be configured to detect and report increased amounts of a favorable gas in the borehole 616. The resulting output signal 646 may then inform the operator where a particular type or quantity of favorable gas is found in the borehole 616 and, as a result, at least one drilling parameter may be adjusted in response thereto. For example, the operator may alter the geosteering of the drill bit 614 so that the borehole 616 may be drilled or formed substantially in that stratum or zone. In vertical boreholes 616, the well operator may be able to log the area of the borehole 616 where a high gas content is detected and, at a later time, return to that location and complete the borehole 616 at that location such that the hydrocarbons residing in the formation 618 at that location may be effectively produced with greater efficiency.

The third optical computing device 640c may also be configured to detect hazardous, corrosive, or otherwise toxic gases (i.e., $H_2S$, methane, etc.) that may be entrained in the drilling fluid 622. The resulting output signal 646 in such cases may inform an operator via the peripheral devices 648 of the presence of such gases, and the operator may then act to remedy the situation. In other embodiments, the signal processor 642 may autonomously act to remedy the situation, such as by shutting down the well or adding $H_2S$ scavengers or other additives to the drilling fluid 622 via the hopper 638 to remedy the situation. For example, as briefly mentioned above, the signal processor 642 may be communicably coupled to an automated control system (not shown) that may be configured to undertake the required corrective action.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMs, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

It should also be noted that the various drawings provided herein are not necessarily drawn to scale nor are they, strictly speaking, depicted as optically correct as understood by those skilled in optics. Instead, the drawings are merely illustrative in nature and used generally herein in order to supplement understanding of the systems and methods provided herein. Indeed, while the drawings may not be optically accurate, the conceptual interpretations depicted therein accurately reflect the exemplary nature of the various embodiments disclosed.

Embodiments disclosed herein include Embodiment A, Embodiment B, and Embodiment C.

Embodiment A

A system that includes: a flow path circulating a drilling fluid into and out of a borehole penetrating a subterranean formation during a drilling operation, wherein the flow path includes a degasser that includes a drilling fluid inlet, a drilling fluid outlet, and a gas outlet, and wherein the gas outlet is fluidly coupled to a gas analysis device configured to produce a first output signal, a second output signal, and a third output signal corresponding to a concentration of a first gas, a second gas, and a third gas, respectively; a first integrated computational element and a second integrated computational element arranged along the flow path prior to the drilling fluid inlet of the degasser and configured to optically interact with the drilling fluid and generate a fourth output signal and a fifth output signal, respectively, corresponding to a concentration of the first gas present in the drilling fluid and a concentration of the second gas present in the drilling fluid, respectively; a signal processor communicably coupled to the first integrated computational element, the second integrated computational element, and the gas analysis device, wherein the signal processor is configured to (1) receive the first output signal, the second output signal, the third output signal, the fourth output signal, and the fifth output signal, (2) calculate a calibration factor based on an analysis of the first output signal relative to the fourth output signal and the second output signal relative to the fifth output signal, and (3) apply the calibration factor to the third output signal to produce a calibrated output signal corresponding to a calibrated concentration of the third gas.

Embodiment A may have one or more of the following additional elements in any combination: Element A1: the system further including a third integrated computational element and a fourth integrated computational element arranged between the gas outlet of the degasser and the gas analysis device and configured to (1) optically interact with a gas composition extracted from the drilling fluid by the degasser and (2) generate a sixth output signal and a seventh output signal, respectively, corresponding to a concentration of the first gas present in the gas composition and a concentration of the second gas present in the gas composition, respectively; and wherein the signal processor is configured to (1) receive the sixth output signal and the seventh output signal and (2) further calculate the calibration factor based on an analysis of the first output signal relative to the fourth and sixth output signals and the second output signal relative to the fifth and seventh output signals; Element A2: the system further including one or more peripheral devices communicably coupled to the signal processor and configured to receive the calibrated output signal from the signal processor and report the calibrated concentration of the third gas to a well operator; Element A3: Element A2 wherein the one or more peripheral devices are further configured to adjust one or more parameters of the drilling operation in response to the calibrated concentration of the third gas; Element A4: wherein at least one of the first gas and the second gas is not from the subterranean formation; Element A5: wherein the first gas and the second gas are from the subterranean formation; Element A6: wherein the first gas or the second gas is methane; and Element A7: wherein the first gas or the second gas is carbon dioxide.

By way of non-limiting example, exemplary combinations applicable to Embodiment A include: Element A5 in combination with Element A6 and optionally Element A7, Element A5 in combination with Element A7, Element A4 in combination with Element A7, at least one of Elements A1-A3 in combination with any of the foregoing, and Element A1 in combination with Element A2 and optionally Element A3.

Embodiment B

A method that includes: circulating a drilling fluid within a flow path that extends into and out of a borehole penetrating a subterranean formation during drilling operations and includes a degasser having a drilling fluid inlet, a drilling fluid outlet, and a gas outlet; generating a first output signal, a second output signal, and a third output signal corresponding to a concentration of a first gas, a second gas, and a third gas with a gas analysis device fluidly coupled to the gas outlet of the degasser; generating a fourth output signal with a first integrated computational element and a fifth output signal with a second integrated computational element arranged along the flow path prior to the drilling fluid inlet of the degasser corresponding to a concentration of the first gas present in the drilling fluid and a concentration of the second gas present in the drilling fluid, respectively; receiving the first output signal, the second output signal, the third output signal, the fourth output signal, and the fifth output signal with a signal processor communicably coupled to the gas analysis device, the first optical computing device, and the second optical computing device; calculating a calibration factor based on an analysis of the first output signal relative to the fourth output signal and the second output signal relative to the fifth output signal; and applying the calibration factor to the third output signal to produce a calibrated output signal corresponding to a calibrated concentration of the third gas.

Embodiment B may have one or more of the following additional elements in any combination: Element B1: the method further including generating a sixth output signal with a third integrated computational element and a seventh output signal with a fourth integrated computational element arranged between the gas outlet of the degasser and the gas analysis device corresponding to a concentration of the first gas present in a gas composition extracted from the drilling fluid by the degasser and a concentration of the second gas present in the gas composition, respectively; receiving the sixth output signal and the seventh output signal with the signal processor communicably coupled to the third optical computing device and the fourth optical computing device; and further calculating the calibration factor based on an analysis of the first output signal relative to the fourth and sixth output signals and the second output signal relative to the fifth and seventh output signals; Element B2: the method including Element B1 and further including conveying the calibrated output signal to one or more peripheral devices; and adjusting one or more drilling or completion parameters in response to the calibrated concentration of the third gas; Element B3: wherein at least one of the first gas and the second gas is not from the subterranean formation; Element B4: wherein the first gas and the second gas are from the subterranean formation; Element B5: wherein the first gas or the second gas is methane; Element B6: wherein the first gas or the second gas is carbon dioxide; Element B7: the method further including conveying the calibrated output signal to one or more peripheral devices; and adjusting one or more drilling or completion parameters in response to the calibrated concentration of the third gas; Element B8: Element B7 wherein adjusting the one or more drilling or completion parameters comprises altering the geosteering of a drill bit; and Element B9: Element B7 wherein adjusting the one or more drilling or completion parameters comprises at least one of changing a cementing program, changing a casing program, changing a casing design, optimizing placement of downhole perforations, sliding sleeves, and slotted liners, and optimizing isolation of zones from which production is not required.

By way of non-limiting example, exemplary combinations applicable to Embodiment B include: Element B4 in combination with Element B5 and optionally Element B6, Element B4 in combination with Element B6, Element B3 in combination with Element B6, at least one of Elements B3-B6 in combination with at least one of Elements B7-B9, at least one of Elements B3-B6 in combination with at least one of Elements B1-B2, Element B1 in combination with Element B2; and Element B1 in combination with Element B7 and optionally at least one of Elements B8-B9.

Embodiment C

A method that includes: circulating a drilling fluid within a flow path that extends into and out of a borehole penetrating a subterranean formation during a drilling operation and includes a degasser having a drilling fluid inlet, a drilling fluid outlet, and a gas outlet; generating a first output signal, a second output signal, and a third output signal corresponding to a concentration of a first gas, a second gas, and a third gas with a gas analysis device fluidly coupled to the gas outlet of the degasser; generating a fourth output signal with a first integrated computational element and a fifth output signal with a second integrated computational element arranged along the flow path prior to the drilling fluid inlet of the degasser corresponding to a concentration of the first gas present in the drilling fluid and a concentration of a fourth gas present in the drilling fluid, respectively; receiving the first output signal, the second output signal, the third output signal, the fourth output signal, and the fifth output signal with a signal processor communicably coupled to the gas analysis device, the first optical computing device, and the second optical computing device; calculating a calibration factor based on an analysis of the first output signal relative to the fourth output signal and the second output signal relative to the fifth output signal; and applying the calibration factor to the third output signal to produce a calibrated output signal corresponding to a calibrated concentration of the third gas.

Embodiment C may have one or more of the following additional elements in any combination: Element C1: wherein at least one of the first gas and the second gas is not from the subterranean formation; Element C2: wherein the first gas and the second gas are from the subterranean formation; Element C3: wherein the first gas or the second gas is methane; Element C4: wherein the first gas or the second gas is carbon dioxide; and Element C5: the method further including conveying the calibrated output signal to one or more peripheral devices.

By way of non-limiting example, exemplary combinations applicable to Embodiment C include: Element C2 in combination with Element C3 and optionally Element C4, Element C2 in combination with Element C4, Element C2 in combination with Element C4, and at least one of Elements C1-C4 in combination with Element C5.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively described herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. A system comprising:
a flow path circulating a drilling fluid into and out of a borehole penetrating a subterranean formation during a drilling operation, the flow path comprising a degasser that includes a drilling fluid inlet, a drilling fluid outlet, and a gas outlet, and
the gas outlet being fluidly coupled to a gas analysis device configured to produce a first output signal, a second output signal, and a third output signal corresponding to a concentration of a first gas, a second gas, and a third gas, respectively;
a first integrated computational element and a second integrated computational element arranged along the flow path prior to the drilling fluid inlet of the degasser and configured to optically interact with the drilling fluid and generate a fourth output signal and a fifth output signal, respectively, corresponding to a concentration of the first gas present in the drilling fluid and a concentration of the second gas present in the drilling fluid, respectively;
a signal processor communicably coupled to the first integrated computational element, the second integrated computational element, and the gas analysis device,
the signal processor being configured to (1) receive the first output signal, the second output signal, the third output signal, the fourth output signal, and the fifth output signal, (2) calculate a calibration factor based on an analysis of the first output signal relative to the fourth output signal and the second output signal relative to the fifth output signal, and (3) apply the calibration factor to the third output signal to produce a calibrated output signal corresponding to a calibrated concentration of the third gas.

2. The system of claim 1 further comprising:
a third integrated computational element and a fourth integrated computational element arranged between the gas outlet of the degasser and the gas analysis device and configured to (1) optically interact with a gas composition extracted from the drilling fluid by the degasser and (2) generate a sixth output signal and a seventh output signal, respectively, corresponding to a concentration of the first gas present in the gas composition and a concentration of the second gas present in the gas composition, respectively; and
wherein the signal processor is configured to (1) receive the sixth output signal and the seventh output signal and (2) further calculate the calibration factor based on an analysis of the first output signal relative to the fourth and sixth output signals and the second output signal relative to the fifth and seventh output signals.

3. The system of claim 1 further comprising:
one or more peripheral devices communicably coupled to the signal processor and configured to receive the calibrated output signal from the signal processor and report the calibrated concentration of the third gas to a well operator.

4. The system of claim 3, wherein the one or more peripheral devices are further configured to adjust one or more parameters of the drilling operation in response to the calibrated concentration of the third gas.

5. The system of claim 1, wherein at least one of the first gas and the second gas is not from the subterranean formation.

6. The system of claim 1, wherein the first gas and the second gas are from the subterranean formation.

7. The system of claim 1, wherein the first gas or the second gas is methane.

8. The system of claim 1, wherein the first gas or the second gas is carbon dioxide.

9. A method, comprising:
circulating a drilling fluid within a flow path that extends into and out of a borehole penetrating a subterranean formation during drilling operations and includes a degasser having a drilling fluid inlet, a drilling fluid outlet, and a gas outlet;
generating a first output signal, a second output signal, and a third output signal corresponding to a concentration of a first gas, a second gas, and a third gas with a gas analysis device fluidly coupled to the gas outlet of the degasser;
generating a fourth output signal with a first integrated computational element and a fifth output signal with a second integrated computational element arranged along the flow path prior to the drilling fluid inlet of the degasser corresponding to a concentration of the first gas present in the drilling fluid and a concentration of the second gas present in the drilling fluid, respectively;
receiving the first output signal, the second output signal, the third output signal, the fourth output signal, and the fifth output signal with a signal processor communicably coupled to the gas analysis device, the first optical computing device, and the second optical computing device;
calculating a calibration factor based on an analysis of the first output signal relative to the fourth output signal and the second output signal relative to the fifth output signal; and
applying the calibration factor to the third output signal to produce a calibrated output signal corresponding to a calibrated concentration of the third gas.

10. The method of claim 9 further comprising:
conveying the calibrated output signal to one or more peripheral devices; and
adjusting one or more drilling or completion parameters in response to the calibrated concentration of the third gas.

11. The method of claim 10, wherein adjusting the one or more drilling or completion parameters comprises altering the geosteering of a drill bit.

12. The method of claim 10, wherein adjusting the one or more drilling or completion parameters comprises at least one of changing a cementing program, changing a casing program, changing a casing design, optimizing placement of downhole perforations, sliding sleeves, and slotted liners, and optimizing isolation of zones from which production is not required.

13. The method of claim 9 further comprising:
generating a sixth output signal with a third integrated computational element and a seventh output signal with a fourth integrated computational element arranged between the gas outlet of the degasser and the gas analysis device corresponding to a concentration of the first gas present in a gas composition extracted from the drilling fluid by the degasser and a concentration of the second gas present in the gas composition, respectively;
receiving the sixth output signal and the seventh output signal with the signal processor communicably coupled to the third optical computing device and the fourth optical computing device; and
further calculating the calibration factor based on an analysis of the first output signal relative to the fourth and sixth output signals and the second output signal relative to the fifth and seventh output signals.

14. The method of claim 13 further comprising:
conveying the calibrated output signal to one or more peripheral devices; and
adjusting one or more drilling or completion parameters in response to the calibrated concentration of the third gas.

15. The method of claim 9, wherein at least one of the first gas and the second gas is not from the subterranean formation.

16. The method of claim 9, wherein the first gas and the second gas are from the subterranean formation.

17. The method of claim 9, wherein the first gas or the second gas is methane.

18. The method of claim 9, wherein the first gas or the second gas is carbon dioxide.

19. A method, comprising:
circulating a drilling fluid within a flow path that extends into and out of a borehole penetrating a subterranean formation during drilling operations and includes a degasser having a drilling fluid inlet, a drilling fluid outlet, and a gas outlet;
generating a first output signal, a second output signal, and a third output signal corresponding to a concentration of a first gas, a second gas, and a third gas with a gas analysis device fluidly coupled to the gas outlet of the degasser;
generating a fourth output signal with a first integrated computational element and a fifth output signal with a second integrated computational element arranged along the flow path prior to the drilling fluid inlet of the degasser corresponding to a concentration of the first gas present in the drilling fluid and a concentration of a fourth gas present in the drilling fluid, respectively;
receiving the first output signal, the second output signal, the third output signal, the fourth output signal, and the fifth output signal with a signal processor communicably coupled to the gas analysis device, the first optical computing device, and the second optical computing device;
calculating a calibration factor based on an analysis of the first output signal relative to the fourth output signal and the second output signal relative to the fifth output signal; and applying the calibration factor to the third output signal to produce a calibrated output signal corresponding to a calibrated concentration of the third gas.

20. The method of claim 19, wherein the fourth gas is methane and the second gas is ethane.

* * * * *